United States Patent [19]
Traub et al.

[11] Patent Number: 5,427,111
[45] Date of Patent: Jun. 27, 1995

[54] RECEIVER FOR DIFFERENTIAL SIGNALS WITH MEANS FOR ADJUSTING A FLOATING GROUND STATE

[75] Inventors: Stefan Traub, Schoenaich; Heinz Sommer, Boeblingen, both of Germany

[73] Assignee: Hewlett Packard Company, Palo Alto, Calif.

[21] Appl. No.: 160,438

[22] Filed: Dec. 1, 1993

[30] Foreign Application Priority Data

Mar. 20, 1993 [EP] European Pat. Off. ............ 93104602

[51] Int. Cl.⁶ ............................................. A61B 5/0428
[52] U.S. Cl. ........................................ 128/696; 128/902
[58] Field of Search ................................. 128/696, 902

[56] References Cited

U.S. PATENT DOCUMENTS

| | | | |
|---|---|---|---|
| 3,587,562 | 6/1971 | Williams | 128/902 |
| 4,164,215 | 8/1979 | Finlayson et al. | 128/696 |
| 4,243,044 | 1/1981 | Blancke | 128/696 |
| 5,002,063 | 3/1991 | Haner | 128/696 |

FOREIGN PATENT DOCUMENTS 0165141  12/1985  .

OTHER PUBLICATIONS

"High–Quality Recording of Bioelectric Events, Part 2 Low–noise, low–power multichannel amplifier Design", Medical & Biological Engineering & Computing, vol. 29, No. 4, Jul., 91, pp. 433–439.

"Extracellular Amplifier with Bootstrapped Input Stage Results in High Common–Mode Rejection", Medical & Biological Engineering & Computing, G. Mpitsos, vol. 19, No. 5, Sep. 81, one page European Search Report for Application No. EP 93 10 4602 dated Aug. 25, 1993.

Primary Examiner—William E. Kamm

[57] ABSTRACT

A receiver or preamplifier for differential signals, in particular electrocardiogram signals, includes n electrodes to provide at least one signal at an acceptable common mode rejection ratio, even if the subject to which the electrodes are applied has a different ground potential than the assigned monitor. This is achieved by two current sources which are controlled by a sum signal representing a sum of the electrode signals, said current sources injecting a corresponding current into the electrodes.

11 Claims, 6 Drawing Sheets

RECEIVER FOR DIFFERENTIAL SIGNALS WITH MEANS FOR ADJUSTING A FLOATING GROUND STATE

FIELD OF THE INVENTION

The present invention relates to a receiver for differential signals, in particular biological signals, comprising at least two electrode contact points. More specifically, the invention relates to receiver circuitry used in electrocardiogram (ECG) amplifiers.

BACKGROUND OF THE INVENTION

Basically, the electrocardiogram is the most important physiological parameter for patient monitoring. However, the pick-up of ECG signals may cause technical problems which are—although identified already a long time ago—not easy to overcome.

The most serious problem is caused by the fact that the patient may, for safety reasons, not be connected with the ground potential of the monitor. ECG monitors provide, in general, means for galvanic separation of the patient, such as transformers, optical couplers etc.

The external ECG is not measured against ground, but rather as a differential signal; i.e., one needs at least two leads, and measures the ECG waveform as a voltage difference between these leads. This is just because the patient ground is floating and thus not stable, such that any measurement against monitor ground would reveal useless results. It is understood that more than two leads may be provided as well, in order to obtain multiple waveforms.

The actual differential voltage of an external ECG signal is approximately in the range of 100 $\mu$V to 10 mV. In contrast, the floating ground may cause common mode voltages (i.e., voltages appearing on both ECG leads) of up to (and even exceeding) 100 V. That is, the common voltages may be about $10^3$ to $10^6$ times larger in amplitude than the differential voltages.

It is thus not easy to keep the differential amplifier in its operating range, i.e., to keep its common mode rejection ratio (CMRR) high. A well-known measure therefor is to isolate the differential amplifier galvanically from ground, which results in a CMRR improvement of at most 70 dB. The limiting factor of this first measure is the insulation capacitance of the galvanic separation, which includes the insulation capacitance of the electrical circuitry, and the capacitance of the patient leads with respect to ground. However, the max. 70 dB CMRR are not sufficient to provide a differential signal of acceptable quality.

One has therefore to take other measures as well. One approach widely used in the prior art is the so-called "guard drive". In general, this means that the patient's ground potential is modified such that it approaches the ground potential of the "floating" portion of the pick-up circuitry. More specifically, a signal is derived from the differential signals, e.g. a sum signal, which controls an additional amplifier. The output of the additional amplifier is connected, via a further electrode, with the patient. This concept is also known as "right leg drive".

The contribution of the guard drive is a further improvement of the CMRR of about 20 dB. A limitation of this concept is the loop gain of the guard drive. However, its most serious disadvantage is that an additional electrode has to be provided; for example, 3 ECG electrodes have to be used to obtain a single lead (waveform).

The additional electrode is particularly disadvantageous in clinical practice, specifically in terms of handling. However, the additional time required to apply the third (or $(n+1)^{th}$) electrode, its cost and the confusion by an additional electrode cable is not the only aspect which limits the guard drive concept. Consider, for example, a neonate (newborn baby). A multiplicity of electrodes and sensors are usually applied to the neonate during monitoring in the intensive care unit (e.g., ECG, respiration, blood gases etc.). However, the space on the body of a newborn is limited, such that clinicians often have problems to apply all necessary electrodes.

Thus, there is a strong desire to remove the additional "guard drive" electrode. One has already developed ECG amplifiers without guard drive, so-called "two-lead" amplifiers. Prior art amplifiers of this type employ a differential amplifier with limited input resistance (as opposed to the virtually unlimited input resistance of the differential amplifier in the guard drive concept). The operating point of the differential amplifier is adjusted by means of resistors.

However, the latter concept imposes more stricter demands on the galvanic separation, as compared to the guard drive method. These stricter demands can only be met if the amplifier is integrated into the cable head of the patient cable (which makes the cable more bulky and uncomfortable to handle), and if a transformer of very low stray capacity (<2 pF) is provided for galvanic separation. Both measures also contribute essentially to the costs of the amplifier, and last not least its differential characteristics is also impacted by the limited input resistance.

Thus, there is an ongoing need for a receiver circuit for ECG signals which operates without guard electrode, but still avoids the disadvantages of the known amplifiers.

SUMMARY OF THE INVENTION

The present invention addresses the above needs and provides a reliable, high-performance differential signal receiver which does not require a guard electrode. Its basic features are:

The signals of the at least two electrode contact points are fed to summing means, at least two of the electrode contact points are connected with an output terminal of a controllable current source each, and the amount of current generated by the controllable current sources is controlled by the summing means.

"Electrode contact point" as used herein simply means the receiver's electrical contact to the electrode. The summing means generate a control signal which is fed to current sources. These current sources are connected with the electrode contacts and inject a current (of positive or negative polarity) into the electrode lead and thus into the patient, and the amount of current depends on the control signal generated by the summing means.

It can be shown that the input resistance of such a circuit for differential signals is theoretically infinite, and, as a matter of practice, several ten MegaOhms (e.g., 30 M$\Omega$). That is, the circuit has optimal characteristics for receiving (and/or amplifying) differential signals, like the ECG.

On the other hand, its input resistance is quite low, and may even approach zero, for common mode signals. It is even possible to design the circuit such that the common mode gain is equal to zero.

This is exactly the required functionality of a receiver circuit for differential, particularly differential biological, signals. As the input resistance for common mode signals is approximately zero, a short-circuit is established for these signals, such that they do not appear at the output of the receiver. On the other hand, differential signals are exposed to an unlimited input resistance, and are thus completely transmitted.

The invention has the outstanding advantage that no guard drive is required, but that it nevertheless provides optimal electrical characteristics for the measurement of differential signals. In particular, an ECG waveform may be obtained with two electrodes only. Of course, in case more electrodes (say, n electrodes) are provided, it will also be possible to obtain more than one waveform. This is in contrast to the guard drive approach which always required (n+1) electrodes.

Likewise, the invention is not subject to the restrictions of prior attempts to omit the guard electrode. In particular, the new receiver has not to be integrated into the cable head of the patient cable, nor is there a need for a transformer with extremely low stray capacitance. Another related advantage is that its electrical characteristics is not dependent on the spectral components of the differential, or the common mode signals. To some extent, one could say that the present invention uses the signal leads to drive a patient to a ground It is understood that the present invention, although primarily designed for application in the field of electrocardiogram recording, is useful to record other differential biological signals as well, and even differential signals of non-biological origin. In general, it may be used in every embodiment wherein it is desired to obtain differential signals from a floating subject, or to connect two or more devices via a ground-free (floating) connection, or the like.

Whereas the invention has heretofore been characterized as a "receiver for differential signals", it is understood that it could also be characterized as a "differential amplifier".

The controllable current sources may include any design measures known to skilled people. In particular, whereas one contact terminal of said current sources is connected with the respective electrode contact points, their second contact terminals may advantageously be connected with a constant potential, such as (floating) ground. In a preferred embodiment, the current sources include two transistors of opposite characteristics connected in series. "Opposite characteristics" as used herein means, e.g., a combination of a pnp- and an npn-transistor (bipolar transistors), or a combination of an n-channel-FET and a p-channel-FET (field effect transistors).

A bioelectric amplifier which includes current sources is disclosed in "MEDICAL & BIOLOGICAL ENGINEERING & COMPUTING", volume 19, no. 4, July 1991, Stevenage, GB, pages 433 to 439. The article in this journal, "High-quality recording of bioelectric events" by Metting et al., discloses two current sources which drive two amplifying transistors. However, the current sources do not act on the electrodes and are therefore not suited to shift the potential of a patient close to a floating ground. The same journal contains in its volume 19, no. 5, September 1981, pages 657 to 658 a publication by Mpitsos, "Extracellular amplifier with bootstrapped input stage results in high common-mode rejection", wherein two current sources are used to alter the supply voltage of operational amplifiers. Again, the current sources do not act on the electrode inputs.

The summing means may be an analog or digital adder. However, in the preferred embodiment, it is simply a series connection of two resistors. If more than two electrodes are provided, all of the resistors may be connected with a star point, wherein the star point provides the desired sum. The resistors have preferably all the same resistance, although resistors with different resistances may be provided as well, in order to obtain a weighted sum.

The obtained sum signal is then used to control the current sources. Preferably, the sum signal is fed to an amplifier, wherein the output of the amplifier, in turn, is fed to the control input of the current sources (the term "amplifier" as used herein covers not only circuits with a gain >1, but also circuits with a gain smaller than or equal to unity. In particular, one may consider to use a voltage follower with unity gain, the primary characteristics of which is its high input impedance and low output impedance).

Another option is to apply different gains to the sum signal, prior to feeding it to the controllable current sources. That is, the control signal fed to the first current source is different from the control signal fed to the second current source, just because the control signals have been amplified at a different amount of gain. This possibility is particularly helpful if the source impedances of the voltage sources which generate the ECG signals (i.e., the virtual sources of the patient) are not equal. The IEC, a technical standard, even requires tests at unsymmetric source impedances. A related problem exists when cable resistors, e.g. 1 k$\Omega$ resistors, are integrated into the electrode cables which prevent the circuitry against the high interfering voltages of defibrillators or electro-surgery, and when these cable resistors are not exactly equal. However, one can show that it is still possible to obtain a common mode gain of zero, even in the case of unsymmetric source impedances or unsymmetric cable resistors, provided one applies different gains to the sum signal. In general, one could say that the control signal fed to the first current source is $\alpha * U_{sum}$, wherein $\alpha$ is the gain and $U_{sum}$ the sum signal, and that the control signal fed to the second current source is $\beta * U_{sum}$. A common mode gain of zero can be obtained if $\alpha \# \beta$.

It would, of course, be possible to provide different amplifiers, with different gains, for this purpose. However, the preferred solution is a multiplier disposed between the output of the summing means (or an amplifier) and one controllable current source. This is a very effective and inexpensive measure, as the other current source does not require such a multiplier (although the invention relates also to embodiments with multiple multipliers). The multiplier may be controlled, either manually or on an automatic basis, to provide for minimum common mode gain, even in the case of unsymmetric impedances.

The controllable current sources according to the present invention may also be useful for yet another purpose. It is known that, in clinical practice, not only the ECG of patients is monitored, but often also their respiration. Measurement of the respiration (impedance pneumography) requires that an alternating current is induced into the patient via a first pair of electrodes. A second pair of electrodes measures the voltage drop across the patient's chest. As the induced current is known, one can thus calculate the impedance of the chest, which, in turn, is a function of respiratory activity. However, in order to provide the necessary high common mode rejection ratio of the respiration measurement electrodes, a transformer is used, with all implied drawbacks such as cost, low input impedance and necessity of adjustment.

One would need six electrodes to record the ECG and the respiration, two for the ECG and four for respiration. In order to reduce the number of electrodes, the ECG electrodes have already been used in the past to measure respiration as well, i.e. the alternating voltage drop along the patient's chest. This is possible just because the alternating voltage used for respiration contains different frequency components (some 10 kHz, e.g., 70 kHz), as compared to the ECG. If a transformer is used for respiration measurement (see supra), it has to be decoupled from the ECG, which, in turn, impacts its characteristics.

The present invention provides for an easy way to remove the transformer, with all related advantages. That is, the controllable current sources may be used to induce the alternating current required for respiration measurement. In other words, the current sources are additionally modulated with differential signals (signals of opposite phase), or separate current sources are provided therefor; this does not disturb their functionality as regards the compensation of floating ground variations. Thus, in a preferred embodiment of the invention, signals of opposing polarity and of a frequency higher than the frequency of the electrocardiogram are fed to controllable current sources, in order to induce an alternating current into the patient, particularly for measuring his respiration.

The invention also relates to a method for processing signals, in particular biological signals, including the steps of:

Receiving signals of at least two electrodes;
summing the received signals, in order to obtain a sum signal;
injecting a controllable current into the electrodes; and
controlling the amount of injected current in dependence of the sum signal.

It is understood and expressly noted that the present invention relates to all useful and novel combinations of the above disclosed features, whether alone or in any other or arbitrary combination.

BRIEF DESCRIPTION OF THE DRAWINGS

The invention will now be explained, by means of a non-limiting example, with reference to the accompanying drawings, in which.

DETAILED DESCRIPTION OF THE PREFERRED EMBODIMENTS

Figure 1:
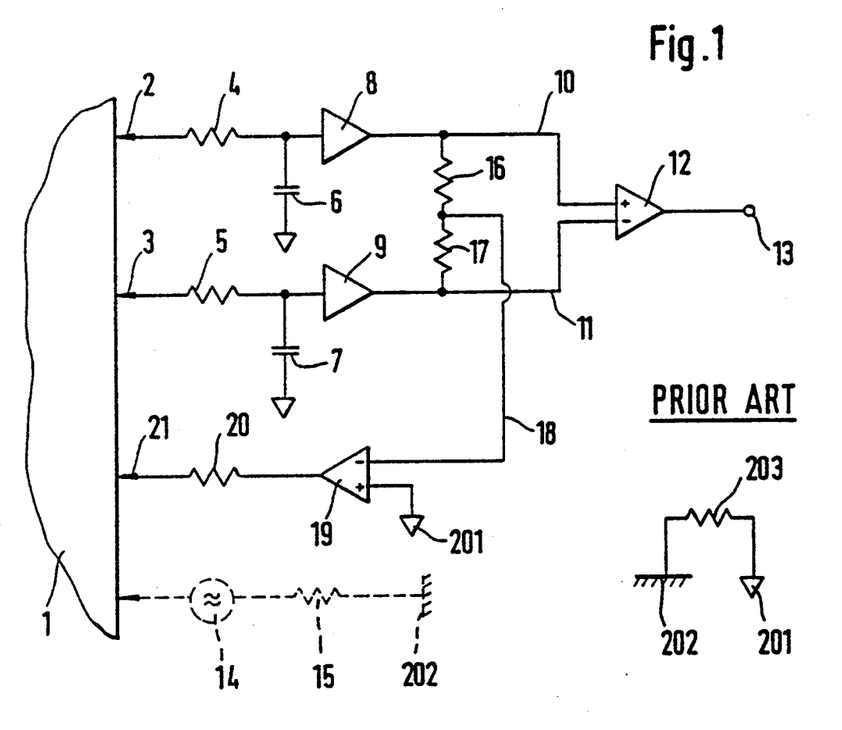
FIG. 1 depicts a prior art ECG preamplifier operating according to the "guard drive" concept.

An ECG (Electrocardiogram) preamplifier according to the prior art is depicted in FIG. 1. This preamplifier uses the "guard drive" concept.

Reference number 1 indicates the patient. A first ECG lead is designated as 2, and a second ECG lead as 3. The signals picked up by the two electrodes are fed, via resistors 4 and 5, and capacitors 6 and 7, respectively, to amplifiers 8 and 9 (which may have a gain of 1 . . . 5). Resistors 4 and 5 stand for the source impedance of the virtual voltage sources of the patient, and, in addition, for any cable resistance. Likewise, capacitors 6 and 7 stand for the cable capacity.

Amplifiers 8 and 9 provide high input resistance, such as most operational amplifiers. Their outputs are fed—via lines 10 and 11—to a differential amplifier 12 which produces—at output 13—a signal representative of the difference between the two signals picked up by electrode leads 2 and 3.

For safety reasons, the patient is electrically isolated from the ground potential of the associated monitor. (Means for providing such galvanic isolation are well-known in the art and thus not shown in detail in FIG. 1. In general, output 13 may be connected with a transformer, an optical coupler or the like.)

That is, the patient's ground potential is different from monitor ground (also called "non-floating ground"). Thus, without additional measures, the voltage difference between patient ground and non-floating ground may amount to several hundred volts. This is indicated by the dotted voltage source 14 and resistor 15 from the patient to ground. The ECG preamplifier has therefore to detect differential signals of some hundred $\mu V$ to some hundred mV which are hidden in a common mode voltage of up to 100 V and even more.

Differential amplifiers which are so sensitive as to detect the above-mentioned differential ECG signal of small amplitude will not be able to handle the large amount of common mode swing. Thus, additional measures have to be taken.

The circuit in FIG. 1 provides two resistors 16 and 17 which produce a signal representative of the sum of the two differential ECG signals on line 18. This signal is fed to an amplifier 19 and, in turn, to patient 1 via a resistor 20. An additional electrode 21 has therefore to be placed on the patient's skin.

The amplified sum signal drives the patient to a potential which is close to a ground called "floating ground"; this is the potential of a floating section of the ECG preamplifier. In FIG. 1, the floating ground is indicated by a triangle (see ref. no. 201), in contrast to monitor ground (or earth potential) 202. It is important to note that there is an additional impedance between monitor ground 202 and floating ground 201, as indicated by impedance 203. This impedance is primarily of capacitive nature and typically 2 pF (Picofarads). However, in case the patient cable is placed near grounded objects, it may amount up to 20 pF.

The effect of the above measure is an improvement in the operating characteristics of the preamplifier. However, an additional electrode 21 has to be used, with all related disadvantages.

Figure 2:
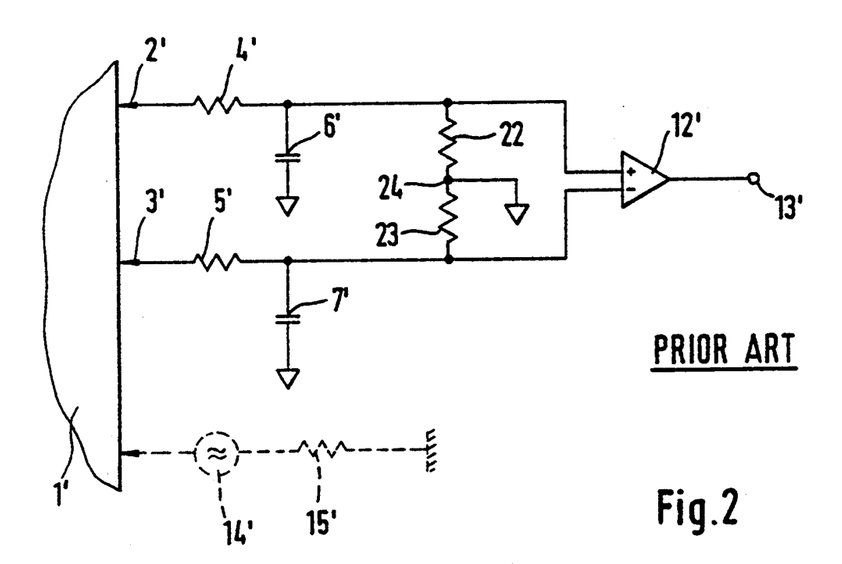
FIG. 2 is another prior art approach with two leads and limited input resistance.

FIG. 2 depicts another prior art approach. Insofar as identical with FIG. 1, the same reference numbers have been used, but with an additional apostrophe instead.

Signals picked up by two electrodes 2' and 3' from a patient 1' are fed, via resistors 4' and 5', and capacitors 6' and 7', respectively, to a differential amplifier 12' which produces an output signal 13'. The patient's voltage to ground, and the related impedance, are designated as 14' and 15'.

One will note that amplifiers 8 and 9 have been omitted in the circuit according to FIG. 2. Further, 1 MΩ resistors 22 and 23 have a different function than resistors 16 and 17 in FIG. 1; this is the reason that different reference numbers have been used. In fact, the interconnection (star) point 24 between resistors 22 and 23 is not connected with a guard electrode, but with ground instead.

The function of resistors 22 and 23 is to adjust the operating point of differential amplifier 12'. Although this embodiment does not require a guard electrode, it is evident that the input resistance of this circuit with respect to common mode signals is quite high—this is an undesirable effect, like the fixed proportion between the common mode input resistance and the differential input resistance. Further, the galvanic separation is subject to stricter requirements in this case which makes it necessary to integrate the preamplifier into the cable head of the patient cable.

Figure 3:
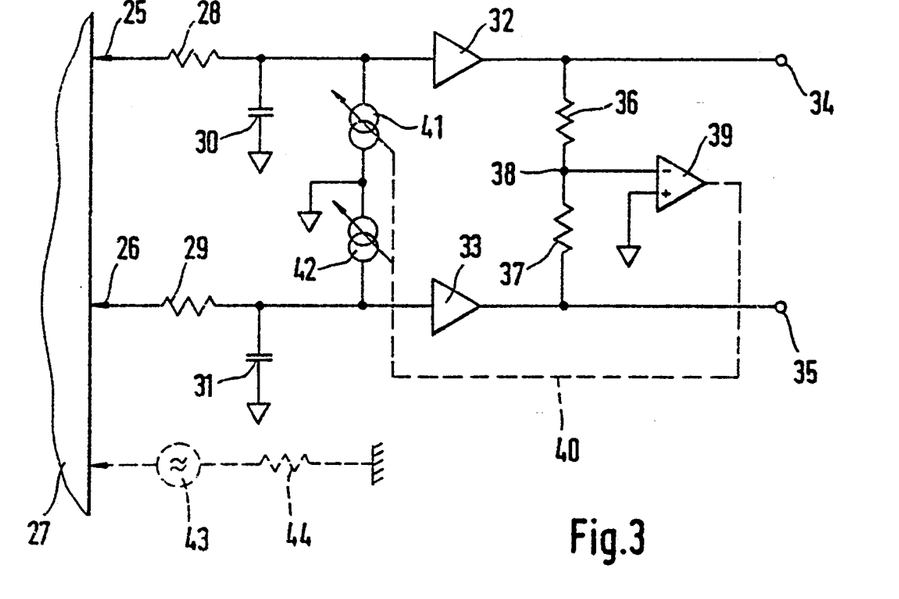
FIG. 3 shows a first embodiment of the present invention.

A first embodiment of the present invention is shown in FIG. 3. Two electrodes 25 and 26 attached to patient 27 feed the ECG signals, via respective resistors 28 and 29, and respective capacitors 30 and 31 (which represent the resistances and capacitances of the patient and the patient cable) to amplifiers 32 and 33 of high input impedance. Their outputs 34 and 35 are (not shown in FIG. 3) further connected with a differential amplifier, such as differential amplifiers 12 and 12' in FIGS. 1 and 2.

Two resistors 36 and 37 feed the ECG signals to a star point 38. It is evident that amplifiers 32 and 33 primarily serve as impedance transformers, such that resistors 36 and 37 do not put a load on the electrodes; in other words, amplifiers 32 and 33 have a very high input impedance, and low output impedance. Star point 38 is connected with the inverting input of an amplifier 39 whose non-inverting input is connected with (floating) ground. This amplifier generates a feedback signal, or control signal, which is fed—via line 40—to current sources 41 and 42. Each of the current sources has one terminal connected with the respective ECG lead, and another terminal which is connected to ground. The control signal on line 40 controls the amount of current injected by current sources 41 and 42 into the patient leads.

This circuit arrangement provides extremely high input impedance for differential signals, and very low input impedance for common mode signals, as will be shown later. It is thus not necessary to provide an additional guard electrode, nor is the inventive circuit subject to the restrictions of the preamplifier according to FIG. 2.

Although resistors 36 and 37 preferably have the same resistance, this is not a necessary prerequisite for practicing the present invention. In fact, one may consider to use different resistor values, in order to obtain a weighted sum signal at star point 38. Likewise, the control signals fed to current sources 41 and 42 must not necessarily be identical, although this case is shown in FIG. 3. We will later consider a case wherein different amplification factors are provided for the control signals fed to the current sources.

As in the preceding figures, the patient's voltage and impedance to ground are indicated by dotted voltage source 43, and dotted impedance 44.

Figure 4:
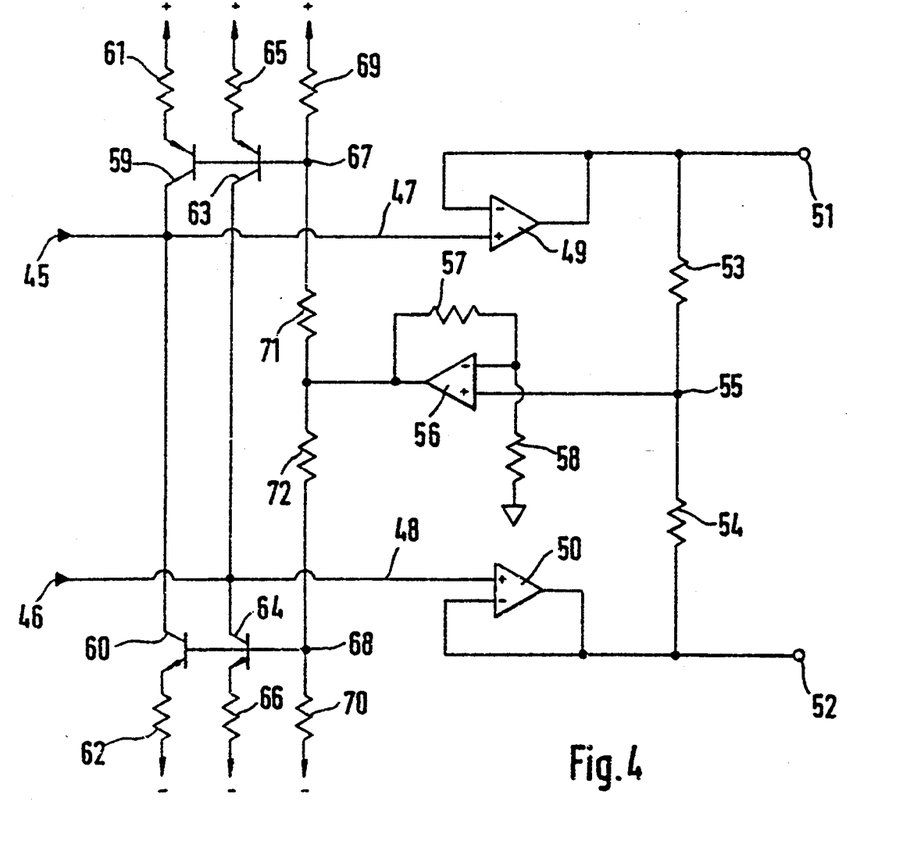
FIG. 4 is an actual circuit used to practice the invention.

The circuit of FIG. 3 has been shown in more or less diagrammatic form, in order to show the basics of the present invention. FIG. 4 depicts an actual embodiment. The two ECG electrodes are designated as 45 and 46. The signals on the two ECG leads are fed, via lines 47 and 48, to the non-inverting inputs of amplifiers 49 and 50. These amplifiers operate as voltage followers, as their feedback loops from their respective outputs to their respective inverting inputs indicate. The output signals on lines 51 and 52 are fed to a further differential amplifying circuit (not shown in FIG. 4).

Resistors 53 and 54—which are both 50 kΩ resistors—connect the two ECG signals with a star point 55. As later calculations will show, the potential at the star point is half the sum of the two ECG signals. Thus, resistors 53 and 54 provide a signal representative of the sum of the two ECG signals.

Star point 55 is connected with the non-inverting input of an operational amplifier 56. This operational amplifier is wired as electrometer amplifier, as indicated by 50 kΩ resistor 57 and 1 kΩ resistor 58. The output of amplifier 56 constitutes a control signal for the current sources, as will be explained now.

The first current source—namely, the current source which drives electrode 45—is basically constituted of a pnp-transistor 59 and an npn-transistor 60, wherein the collectors of these two transistors are connected, and in contact with electrode 45. 100 kΩ resistors 61 and 62 connect their respective emitters with a positive and a negative supply voltage.

Likewise, a pnp-transistor 63, an npn-transistor 64 and two 100 kΩ resistors 65 and 66 constitute the second current source which drives electrode 46. Thus, the collectors of transistors 63 and 64 are in contact with this electrode.

The control inputs of the two current sources are labelled as 67 and 68. These inputs are under control of the signal generated by amplifier 56, namely via a voltage divider including 100 kΩ resistors 69 and 70, as well as 180 kΩ resistors 71 and 72.

Figure 5:
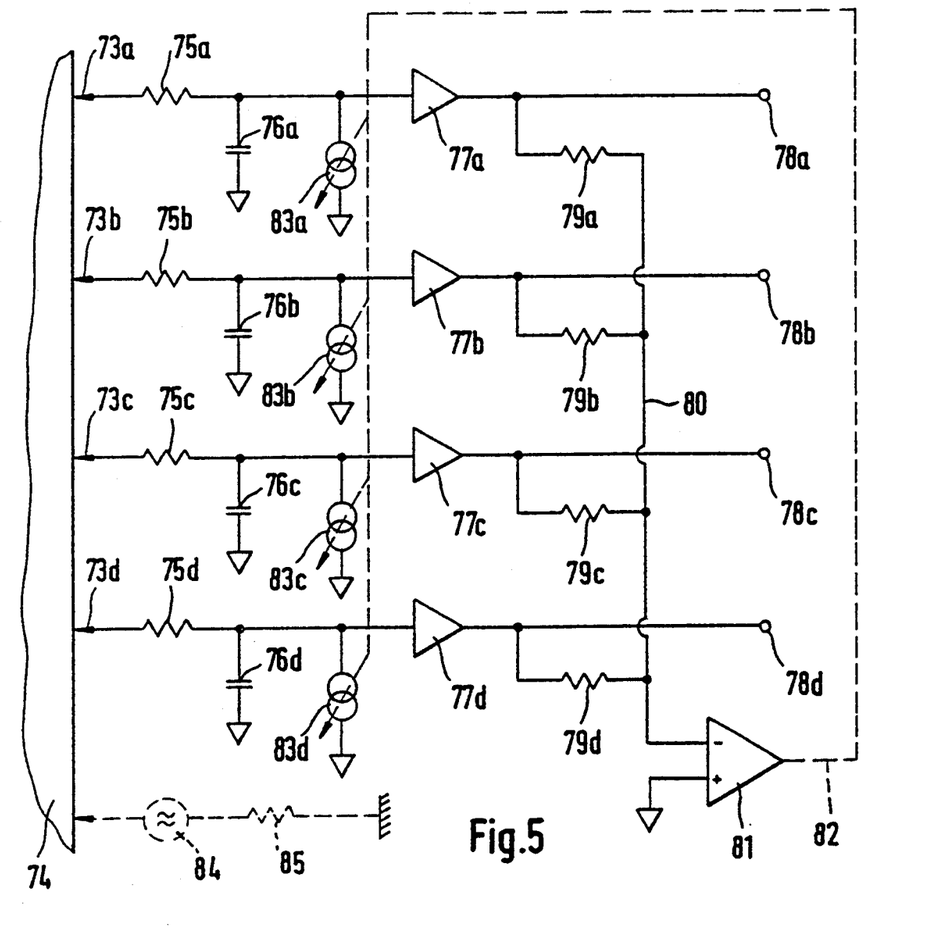
FIG. 5 depicts an embodiment with more than two ECG leads.

An embodiment with more than two—namely four—electrodes is shown in FIG. 5. The electrodes are labelled as 73a to 73d, and applied to a patient 74. The signals picked up by the ECG electrodes are fed—via respective resistors 75a to 75d and capacitors 76a to 76d—to amplifiers, preferably voltage followers 77a to 77d. Their outputs 78a to 78d may be fed to a lead selector switch and a differential amplifier (prior art; not shown in FIG. 5).

Resistors 79a to 79d further connect the outputs of amplifiers 77a to 77d with a star point 80. The potential at this star point is representative of the sum of all ECG signals and fed to the inverting input of an amplifier 81. The output of amplifier 81 (line 82) controls, in turn, current sources 83a to 83d, which inject respective currents into the ECG leads. The patient's voltage and impedance to ground is again indicated by voltage source 84 and impedance 85.

It is understood that the invention covers also other embodiments with more than two electrodes, for example, an embodiment with four electrodes, but only two current sources. Such two current sources provide a sufficient virtual ground, even in case of n electrodes.

Figure 6:
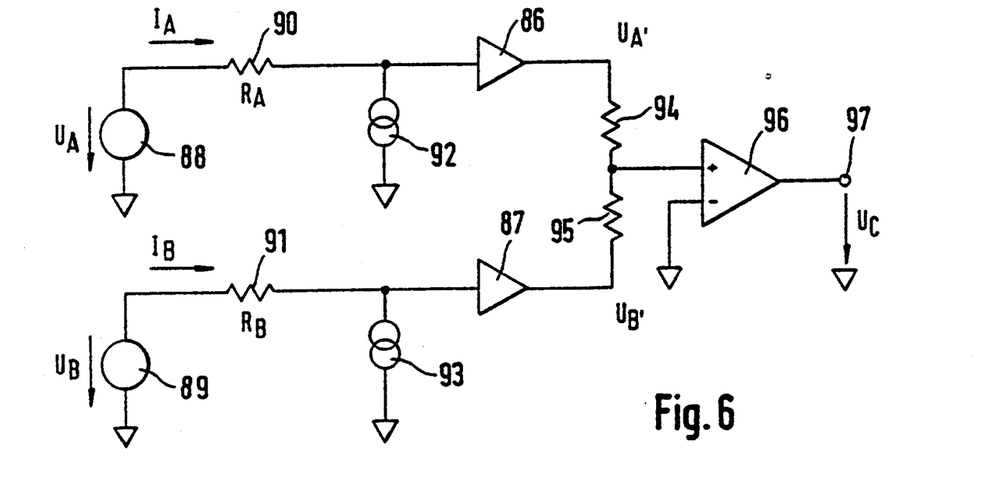
FIG. 6 shows a simplified model of the invention, including the necessary references for voltages and currents, in order to explain its operation.

FIG. 6 shows a simplified model of the invention which will now be used to explain the details of its functionality.

Assume that amplifiers 86 and 87 provide extremely high input impedance, and a gain of 1. In this case, voltages $U_A'$ and $U_B'$ can be expressed as follows:

$$U_A' = U_A - I_A R_A \qquad (1)$$

$$U_B' = U_B - I_B R_B \qquad (2)$$

wherein $U_A$ and $U_B$ are the voltages across voltage sources 88 and 89, and $R_A$ and $R_B$ are the resistances of resistors 90 and 91. $I_A$ and $I_B$ are the currents injected (or sunk) by current sources 92 and 93, respectively.

The outputs of amplifiers 86 and 87 are fed, via resistors 94 and 95, to the non-inverting input of amplifier 96. The voltage generated by this amplifier has been designated as $U_C$ ("C" stands for "control").

The feedback from the output 97 of amplifier 96 to the current sources 92 and 93 has not been drawn in FIG. 6, for graphical purposes. Now, let us assume the most general case wherein different amplification factors are applied to control voltage $U_C$, in order to control the current of current sources 92 and 93, i.e.

$$I_A = \alpha U_C \qquad (3)$$

$$I_B = \beta U_C \qquad (4)$$

wherein $\alpha$ and $\beta$ are the amplification factors.

Given is further the following equation for control voltage $U_C$:

$$U_C = \frac{U_A' + U_B'}{2} \qquad (5)$$

If we substitute these equations into each other, we obtain for the control voltage $$U_C = \frac{U_A + U_B}{2 + \alpha R_A + \beta R_B} \qquad (6)$$

and thus for the currents $$I_A = \alpha \frac{U_A + U_B}{2 + \alpha R_A + \beta R_B} \qquad (7)$$

$$I_B = \beta \frac{U_A + U_B}{2 + \alpha R_A + \beta R_B} \qquad (8)$$

The input impedances are therefore defined as $$R_{in,A} = \frac{U_A}{I_A} = \frac{2 + \alpha R_A + \beta R_B}{\alpha(1 + U_B/U_A)} \qquad (9)$$

$$R_{in,B} = \frac{U_B}{I_B} = \frac{2 + \alpha R_A + \beta R_B}{\beta(1 + U_A/U_B)} \qquad (10)$$

Now let us consider the case of a differential signal. That is, $$U_A = -U_B \qquad (11)$$

One can easily see that the term in brackets in equations (9) and (10) becomes 0, such that the input impedance for differential signals is infinite.

In contrast, if we assume $$U_A = U_B \qquad (12)$$

i.e., the case of common mode signals, we obtain the following expressions for the input impedance:

$$R_{in,A,CM} = \frac{2 + \alpha R_A + \beta R_B}{2\alpha} \qquad (13)$$

$$R_{in,B,CM} = \frac{2 + \alpha R_A + \beta R_B}{2\beta} \qquad (14)$$

Impedances $R_A$ and $R_B$ represent primarily discrete resistors provided for overvoltage protection. If we remove these resistors and replace them with a short-circuit connection, i.e., $R_A = 0$ and $R_B = 0$, and further assume that the amplification factors $\alpha$ and $\beta$ approach infinity, i.e., $\alpha \to \infty$ and $\beta \to \infty$, then the input impedances for common mode signals approach zero, i.e., $R_{in,A,CM} = R_{in,B,CM} \to 0$, which is the desired functionality.

As a more practical example, if we assume $\alpha = \beta = 1/\Omega$ and $R_A = R_B$, equations (13) and (14) simplify to $$R_{in,A,CM} = R_{in,B,CM} = 1\Omega + R_A \qquad (15)$$

which is also the required low input impedance for common mode signals.

Now let us consider the case of unsymmetric, i.e. unequal, source resistances $R_A$ and $R_B$. In this case, we demand $$U_A' = U_B' \qquad (16)$$

for $$U_A = U_B \qquad (17)$$

If we introduce these conditions into equations (1) to (4), we obtain the following condition:

$$\alpha R_A = \beta R_B \qquad (18)$$

For the purpose of simplicity, we set now $\beta = 1/\Omega$ and obtain $$R_B = \alpha R_A \cdot \Omega \qquad (19)$$

Figure 7:
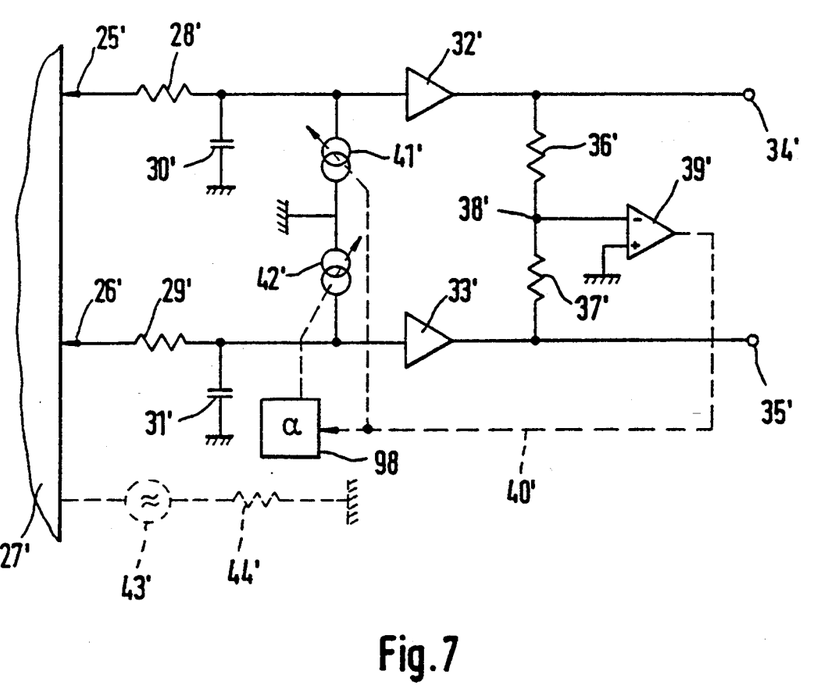
FIG. 7 shows a second embodiment of the invention.

A circuit designed to meet this condition is shown in FIG. 7. This circuit is widely identical with the circuit of FIG. 3, and therefore, the same reference numbers have been used, but with an additional apostrophe. The only difference is that current sources 41' and 42' are not controlled by the same control signal. Instead, a multiplier 98 has been introduced into the control line of current source 42'; in contrast, no such multiplier is provided for the control signal of current source 41'. Multiplier 98 provides exactly the factor which follows from equation (19) and is required to compensate for the different source impedances.

Figure 8:
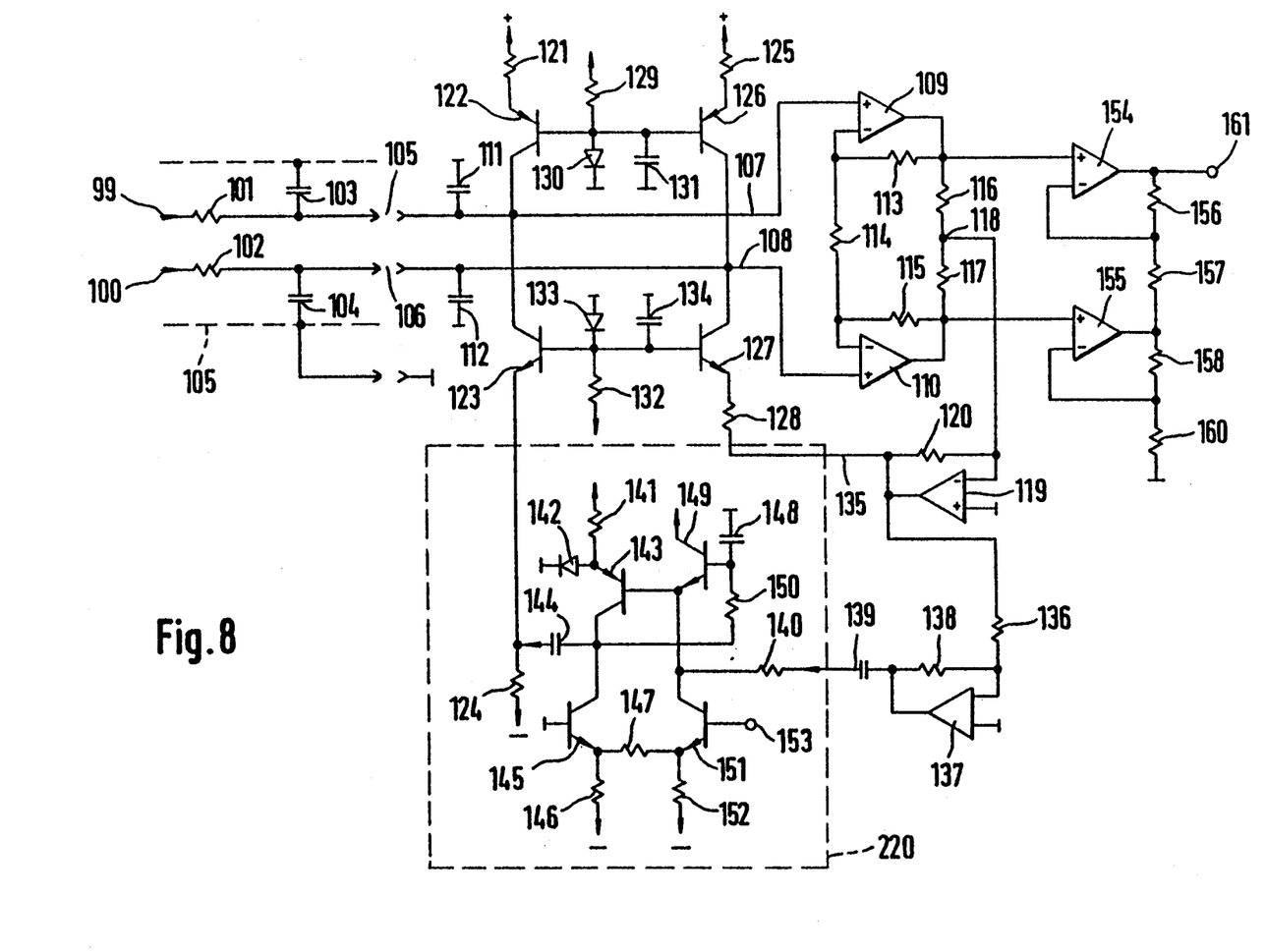
FIG. 8 is an actual circuit according to the second embodiment.

FIG. 8 depicts an actual embodiment of the circuit according to FIG. 7. The patient cable includes two electrodes 99 and 100; two 1 kΩ resistors 101 and 102 establish a protection against defibrillation and/or electro-surgery. Capacitors 103 and 104 represent the cable capacity against shield 105 and are approximately 560 pF.

Reference numbers 105 and 106 stand for the connector jack to the ECG preamplifier. The two ECG signals on leads 107 and 108 are fed to voltage followers 109 and 110; the capacity of these connections with respect to ground is indicated by capacitors 111 and 112 (470 pF each).

Resistors 113, 114 and 115 provide the necessary feedback of voltage followers 109 and 110. The sum signal is generated at the star point between resistors 116 and 117; the signal at the star point (reference number 118) is fed to inverting operational amplifier 119 with feedback resistor 120.

The following components establish the current source driving ECG lead 107: 400 kΩ resistor 121, pnp transistor 122, npn transistor 123 and 404 kΩ resistor 124. Likewise, the current source driving ECG lead 108 is constituted of 400 kΩ resistor 125, pnp transistor 126, npn transistor 127 and 200 kΩ resistor 128. The bases of pnp transistors 122 and 126 are connected with a 40 kΩ resistor 129, a diode 130 and a 100 nF capacitor 131. Likewise, the bases of npn transistors 123 and 127 are connected with 40 kΩ resistor 132, diode 133 and 100 nF capacitor 134.

The control signal generated by operational amplifier 119 (line 135) is directly fed to the current source driving ECG lead 108. In contrast, it does not directly drive the current source related to ECG lead 107; instead, a multiplier has been inserted into this path. The multiplier consists of the following components: 10 kΩ resistor 136, operational amplifier 137, 10 kΩ resistor 138, 100 nF capacitor 139, 200 kΩ resistor 140, 10 kΩ resistor 141, diode 142, pnp transistor 143, 100 nF capacitor 144, npn transistor 145, 400 kΩ resistor 146, 10 kΩ resistor 147, 100 nF capacitor 148, npn transistor 149, 400 kΩ resistor 150, npn transistor 151 and 400 kΩ resistor 152. The control signal which adjusts the multiplication factor is fed to input terminal 153. This signal may either be provided by manual control—e.g. dependent on a previous measurement of source impedances $R_A$ or $R_B$-, or it may be generated on an automatic basis.

It is understood that the multiplier shown in FIG. 8 is of exemplary nature only. It comprises the components in dashed block 220, which may effectively be replaced by other multipliers known in the art.

Operational amplifiers 154 and 155, as well as resistors 156 to 160, provide the difference between the ECG signals which is then available at output terminal 161.

Figure 9:
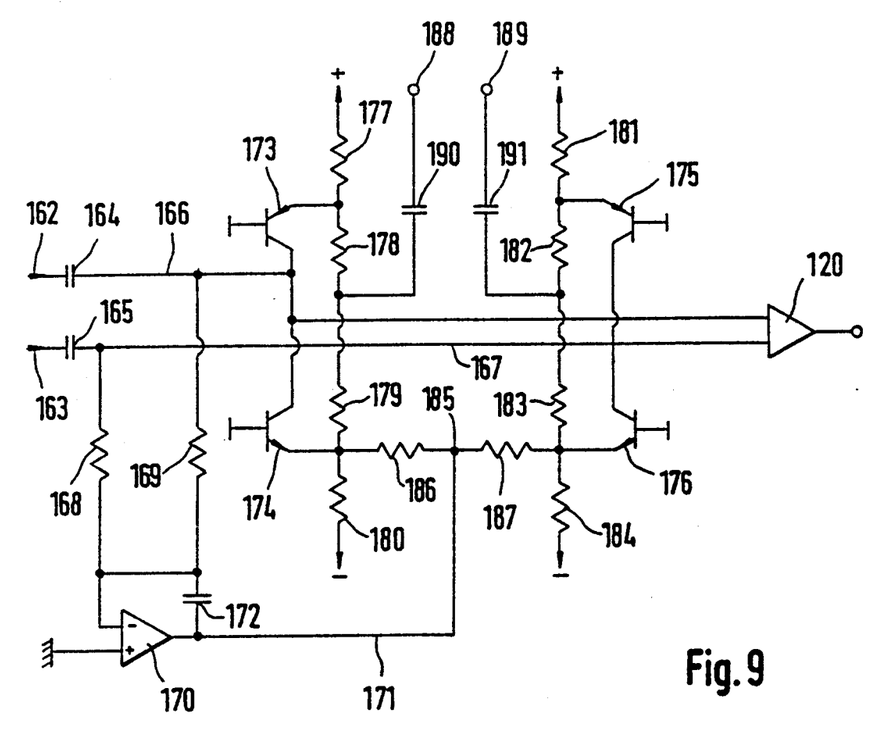
FIG. 9 depicts a third embodiment, specifically suited to induce an additional AC current into the patient.

FIG. 9 depicts a circuit specifically designed to measure the respiration with two electrodes 162 and 163 only.

The two electrodes 162 and 163 are applied to the patient. The signals picked up by these electrodes are fed, via capacitors 164 and 165, to lines 166 and 167. These lines are, via resistors 168 and 169, connected with an operational amplifier 170 which provides the control signal for the current sources (on line 171). A capacitor 172 serves for feedback purposes.

The first current source includes pnp transistor 173 and npn transistor 174. Likewise, pnp transistor 175, and npn transistor 176 constitute the second current source (assigned to line 167). The emitters of the transistors are connected with voltage dividers connected between positive and negative supply voltage and constituted of resistors 177 to 184.

The control signal on line 171 is fed to star point 185 between the two current sources. It is then coupled to the current sources via resistors 186 and 187.

The current sources are controlled by the signals on inputs 188 and 189. These inputs are connected with an AC source which provides an alternating voltage signal of a frequency higher than the components in the electrocardiogram, e.g., 50 kHz or 70 kHz. These signals are of opposite polarity (reversed phase) and are fed, via capacitors 190 and 191, to the current sources, and superimposed with the control signal generated by operational amplifier 170. The current sources thus generate a current which is representative of the control signal, as well as the external AC signal.

The signals on lines 166 and 167 are further fed to a differential amplifier 210 which produces a signal representative of the respiration. The circuit of FIG. 9 thus measures the respiration, and induces the necessary current, with two electrodes only.

The two electrodes 162 and 163 may further be connected with an ECG preamplifier as shown in the preceding figures, e.g., resistors 28 and 29 of the circuit in FIG. 3. Thus, two electrodes are sufficient to measure the ECG, as well as respiration, and to induce the current for respiration measurement. This combination works as long as the frequency used for excitation of the respiration signal is basically different from the frequency components of the ECG signal.

Figure 10:
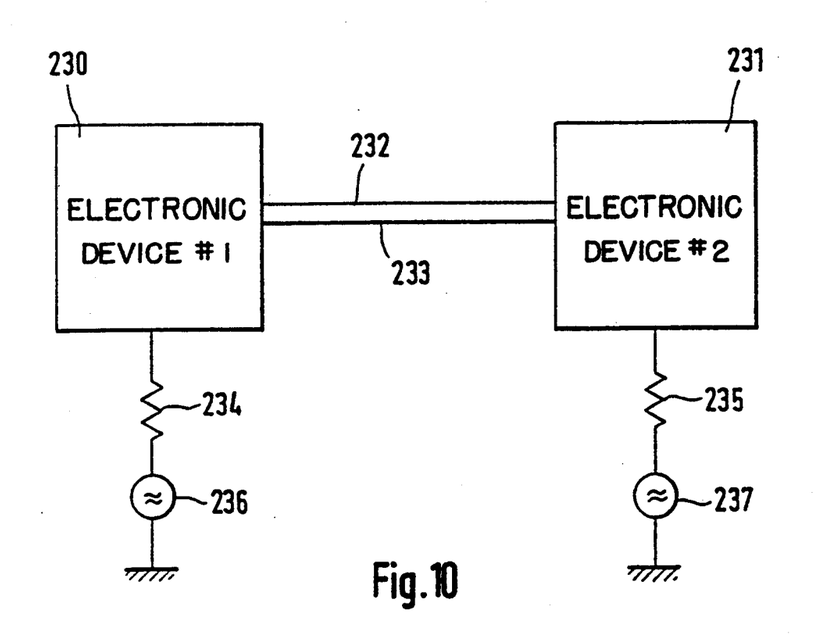
FIG. 10 depicts another application of the present invention.

FIG. 10 depicts another application of the receiver circuit according to the present invention which is unrelated to ECG monitoring. Two electronic devices 230 and 231 of any suitable kind (e.g., terminals, measuring equipment, telephones or the like) are connected via two leads 232 and 233 which are both floating, i.e., not connected with earth potential (see resistors 234 and 235, as well as voltage sources 236 and 237). Both electronic devices 230 and 231 include a receiver circuit according to the present invention; e.g., the circuit of FIG. 3. Such an interconnection compensates for voltage variations, which is an important design criterion, particularly for differential signals with low voltage swing.

In a preferred embodiment, the resistors in the circuit according to FIG. 4 have the following values:

$R_{61}=R_{65}=R_{69}=R_{62}=R_{66}=R_{70}=100$ kΩ
$R_{71}=R_{72}=180$ kΩ
$R_{57}=R_{53}=R_{54}=50$ kΩ
$R_{58}=1$ kΩ

Likewise, the major components in the circuit of FIG. 8 have preferably the following values:

$C_{103}=C_{104}=560$ pF
$C_{111}=C_{112}=470$ pF
$C_{131}=C_{134}=C_{139}=C_{148}=C_{144}=100$ nF
$R_{121}=R_{125}=R_{146}=R_{152}=R_{150}=400$ kΩ
$R_{124}=404$ kΩ
$R_{129}=R_{132}=40$ kΩ
$R_{136}=R_{138}=R_{147}=10$ kΩ
$R_{128}=R_{140}=200$ kΩ and the components in the embodiment of FIG. 9 have preferably the following values:

$C_{164}=C_{165}=10$ nF $C_{172} = C_{190} = C_{191} = 100$ nF
$R_{178} = R_{179} = R_{182} = R_{183} = R_{186} = R_{187} = 10$ kΩ
$R_{177} = R_{180} = R_{181} = R_{184} = 15$ kΩ

We claim:

1. A receiver for differentially detecting biological signals from a patient via first and second electrode contact points, comprising:
   first circuit means connected to said first electrode contact point and having an output;
   second circuit means connected to said second electrode contact point and having an output;
   differential amplifier means connected to each said output from said first circuit means and said second circuit means;
   a first controllable current source connected between said first circuit means and a source of reference potential;
   a second controllable current source connected between said second circuit means and a source of reference potential; and
   summing means coupled to said first and second circuit means and responsive to common mode signals appearing thereon for providing control signals to said first and second controllable current sources, said control signals causing said first and second controllable current sources to inject currents into said first and second circuit means to bring the patient's potential to a predetermined balanced level with respect to said common mode signals.

2. A receiver according to claim 1, wherein circuit means exhibiting a high input impedance are disposed between said electrode contact points and said summing means.

3. A receiver according to claim 1, wherein amplifier means are disposed between said electrode contact points, and said summing means.

4. A receiver according to claim 1, wherein said control signals cause said first and second controllable current sources to insect different current levels into said first and second circuit means.

5. A receiver according to claim 1, wherein at least one of said controllable current sources includes a pnp- and an npn-transistor connected in series.

6. A receiver according to claim 1, wherein said summing means comprises a summing circuit including at least two resistors having a common connection point.

7. A receiver according to claim 6, wherein said summing means further includes an amplifier having an input connected to said common connection point.

8. A receiver according to claim 1, including at least one multiplier circuit disposed between said summing means and at least one of said controllable current sources.

9. A receiver according to claim 1, including means for connecting at least two electrocardiogram electrodes.

10. A receiver according to claim 9, further comprising means for feeding signals of opposing polarity and of a frequency higher than a frequency of said electrocardiogram to said first and second controllable current sources, in order to induce an alternating current into a patient for measuring respiration.

11. A receiver according to claim 10, wherein said signals of opposing polarity are superimposed upon signals generated by said summing means.

* * * * *